United States Patent [19]

Guthrie et al.

[11] 3,962,275
[45] June 8, 1976

[54] 7-OXA STEROIDS
[75] Inventors: Robert William Guthrie, Fairfield; Richard Wightman Kierstead; Ronald Andrew Lemahieu, both of North Caldwell, all of N.J.
[73] Assignee: Hoffmann-La Roche Inc., Nutley, N.J.
[22] Filed: Dec. 11, 1974
[21] Appl. No.: 531,494

Related U.S. Application Data
[62] Division of Ser. No. 259,526, June 5, 1972, Pat. No. 3,869,467.

[52] U.S. Cl. ........................ 260/310 C; 260/310 D; 260/310 R
[51] Int. Cl.$^2$ ........................................ C07D 493/02
[58] Field of Search ................... 260/310 C, 310 D

[56] References Cited
UNITED STATES PATENTS
3,869,467  3/1975  Guthrie et al. ................. 260/310 C OTHER PUBLICATIONS
Guthrie, et al., Chemical Abstracts 78:154986y (1973).

Primary Examiner—Donald B. Moyer
Attorney, Agent, or Firm—Samuel L. Welt; Bernard S. Leon; William H. Epstein

[57] ABSTRACT

7-Oxa steroids which may be substituted in the 3-position with a hydroxy or oxo group or in the 2-position with a hydroxymethylene group or in the 2- and 3-positions with a substituent that forms a 5-membered heterocyclic ring, useful as antigonadotropic agents and a method of preparing these 7-oxa steroids from 3-hydroxy Δ$^5$-steroids including intermediates in this process.

2 Claims, No Drawings

7-OXA STEROIDS

CROSS REFERENCE TO RELATED APPLICATION

This application is a divisional application of U.S. patent application Ser. No. 259,526 filed June 5, 1972, now U.S. Pat. No. 3,869,467 issued March 4, 1975.

SUMMARY OF THE INVENTION

In accordance with this invention, it has been discovered that compounds of the formula:

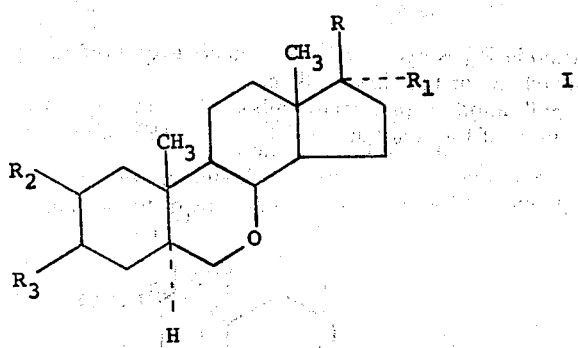

wherein R is hydroxy, a conventional hydrolyzable ester, acetyl, or acetyl ketalized in the 20-position with a lower alkylenedioxy; $R_1$ is hydrogen, hydroxy, a conventional hydrolyzable ester, or lower alkyl; $R_2$ is hydrogen, hydroxymethylene; $R_3$ is oxo, hydroxy, a hydrolyzable ester, lower alkylenedioxy or taken together with $R_2$ and their attached carbon atoms form a pyrazole or isoxazole ring; with the proviso that at least one of R and $R_1$ is other than hydroxy or a conventional hydrolyzable ester;

and compounds of the formula:

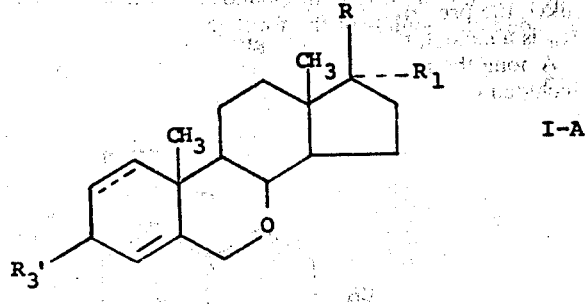

wherein R and $R_1$ are as above; and $R_3'$ is oxo or lower alkylenedioxy; and the dotted bond in the A ring can be optionally hydrogenated;

are useful as antigonadotropic agents.

The compounds of formulae I and I-A are prepared from compounds of the formula:

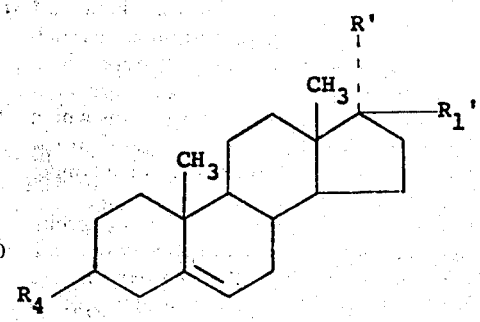

wherein $R_4$ is a hydrolyzable ester, $R'$ is acetyl or a hydrolyzable ester; $R_1'$ is hydrogen, lower alkyl or a hydrolyzable ester with the proviso that at least one of $R'$ and $R_1'$ is other than a hydrolyzable ester.

DETAILED DESCRIPTION OF THE INVENTION

The term "conventional hydrolyzable ester" as used herein denotes the hydrolyzable ester group conventionally employed in the steroid art to protect hydroxy groups. Among the preferred esters are those from hydrocarbon carboxylic acids or phosphoric acids and their salts. The term "hydrocarbon carboxylic acids" defines both substituted and unsubstituted hydrocarbon carboxylic acids. These acids can be completely saturated or possess varying degrees of unsaturation (including aromatic), can be of straight chain, branched chain, or cyclic structure, and preferably contain from 1 to 12 carbon atoms. In addition, they can be substituted by functional groups, for example, hydroxy, alkoxy containing up to 6 carbon atoms, acyloxy containing up to 12 carbon atoms, nitro, amino, halogeno, and the like, attached to the hydrocarbon backbone chain. Typical conventional hydrolyzable esters thus included within the scope of the term and the instant invention are acetate, propionate, butyrate, valerate, caproate, enanthate, caprylate, pelargonate, acrylate, undecenoate, phenoxyacetate, benzoate, phenylacetate, diphenylacetate, diethylacetate, trimethylacetate, t-butylacetate, trimethylhexanoate, methylneopentylacetate, cyclohexylacetate, cyclopentylpropionate, adamantoate, glycolate, methoxyacetate, hemisuccinate, hemiadipate, hemi-$\beta,\beta$-dimethylglutarate, acetoxyacetate, 2-chloro-4-nitrobenzoate, aminoacetate, diethylaminoacetate, piperidinoacetate, $\beta$-chloropropionate, trichloroacetate, $\beta$-chlorobutyrate, dihydrogen phosphate, dibenzyl phosphate, benzyl hydrogen phosphate, sodium benzyl phosphate, cyclohexylammonium benzyl phosphate, sodium phenyl phosphate, sodium ethyl phosphate, di-p-nitrobenzyl phosphate, sodium o-methoxyphenyl phosphate, cyclohexylammonium p-cyanobenzyl phosphate, sodium phenacyl phosphate, benzyl o-carbomethoxyphenyl phosphate and the like.

Among the preferred esters are those derived from lower alkanoic acids such as acetic acid and halo substituted lower alkanoic acids such as trifluoro acetic acids.

As used herein, the term "halogen" comprehends all four halogens such as chlorine, fluorine, bromine and iodine. Alkali metal, as used herein, has its usual meaning and includes such metals as lithium, sodium and potassium. The term "lower alkyl" comprehends both straight and branched chain saturated hydrocarbon moieties having from 1 to 7 carbon atoms such as methyl, ethyl, t-butyl, i-propyl, etc.

Lower alkanoic acids comprehend lower alkane carboxylic acids containing from 2 to 7 carbon atoms such as acetic acid, butyric acid and the like. The term "halo substituted lower alkanoic acids" includes lower alkanoic acids containing from 2 to 7 carbon atoms which are mono, di or tri substituted with a halo group. Among the preferred halo substituted lower alkanoic acids are included trifluoroacetic acid.

The term "lower alkylenedioxy", as used herein, comprehends lower alkylenedioxy moieties containing from 2 to 4 carbon atoms where the two oxygens are attached to the same or different carbon atoms of an alkylene chain such as ethylenedioxy, isopropylidenedioxy, etc. The term "phenyl lower alkyl" designates phenyl lower alkyl moieties wherein lower alkyl is defined as above. Among the preferred phenyl lower alkyl moieties are included, benzyl, phenethyl and phenpropyl.

The compounds of formula I above are characterized by a high degree of antigonadotropic activity. Thus, the compounds of formula I above can be administered internally, for example, orally or parenterally, with dosage adjusted to individual requirements in the form of conventional pharmaceutical preparations; for example, they can be administered in conventional pharmaceutical solid or liquid forms such as tablets, pills, capsules, solutions, suspensions, emulsions or the like. These pharmaceutical preparations can contain conventional pharmaceutical carriers and excipients such as water, talc, corn starch, polyalkylene glycols, emulsifying agents, buffering agents, agents for the adjustment of osmotic pressure, Vaseline and the like. Also, compositions containing an active ingredient of this invention can be subjected to conventional pharmaceutical processes such as sterilization or the like. Also, the pharmaceutical compositions of this invention can contain other active ingredients. Moreover, the endocrinologically active compounds can be administered as feed additives, and for this purpose can be admixed with conventional animal feeds or conventional animal feed premixes. Though, as indicated, the dosage of the endocrinologically useful compounds of this invention should be adjusted to individual needs, i.e., the compounds of formula I above can be administered internally in daily dosage regimens of from about 1 mg./kg. to about 10 mg./kg. per day. The dosages can be administered in unit or divided dosage forms.

The usefulness of the compounds of formula I as antigonadotropic agents is indicated in animals. For example, when these compounds are administered orally for 21 consecutive days to immature rats in a sesame oil solution, there results a decrease in the testes weight of the rats. For example, when compounds such as 7-oxa-17$\beta$-hydroxy-17$\alpha$-methyl- 5$\alpha$-androstano-[3,2-c]-pyrazole and 7-oxa-17$\beta$-hydroxy-17$\alpha$-methyl-5$\alpha$-androstan-3-one, 3-ethylene ketal was administered orally to immature rats for 21 consecutive days in sesame oil solution at a dosage level of 1 mg./kg. per day there resulted a decrease of about 17% in the weight of the rats testes as compared to the control rats which were treated with pure sesame oil.

Among the preferred compounds of formula I are included compounds of the formula:

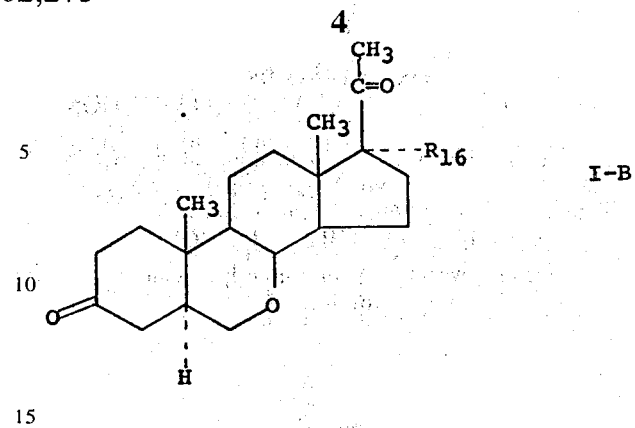

wherein $R_{16}$ is hydroxy, lower alkanoyloxy, preferably acetyloxy, or halo lower alkanoyl.

Still another preferred embodiment of the compounds of formula I are compounds of the formula:

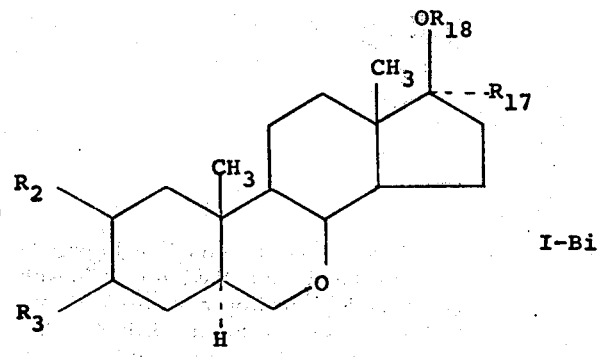

wherein $R_2$ and $R_3$ are as above; $R_{18}$ is hydrogen, lower alkanoyl or halo lower alkanoyl; and $R_{17}$ is hydrogen or lower alkyl.

When $R_{17}$ in the compound of formula I-Bi is lower alkyl, the preferred groups are methyl or ethyl. When $R_{18}$ is alkanoyl, the preferred group is acetyl.

Among the preferred compounds of formula I-A are included compounds of the formula:

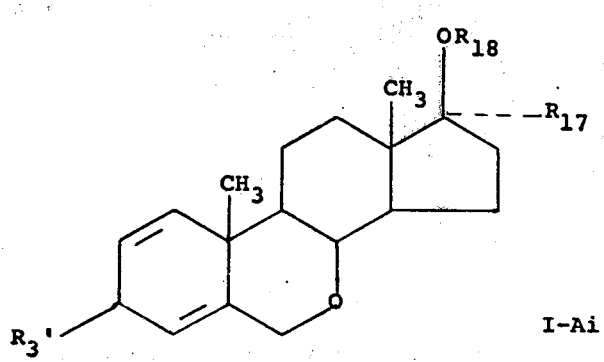

wherein $R_3'$, $R_{17}$ and $R_{18}$ are as above; and compounds of the formula:

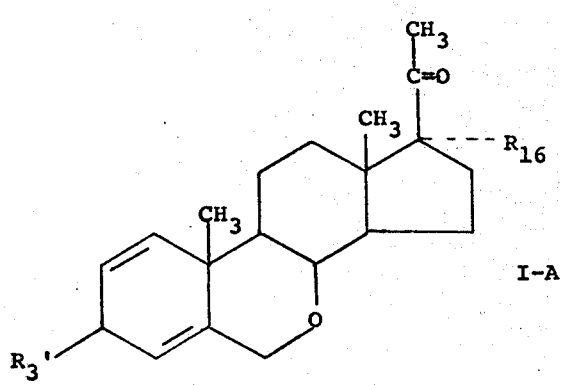

I-Aii wherein $R_3'$ and $R_{16}$ are as above.

The compounds of formula I above are prepared from the compounds of formula II via an intermediate of the formula:

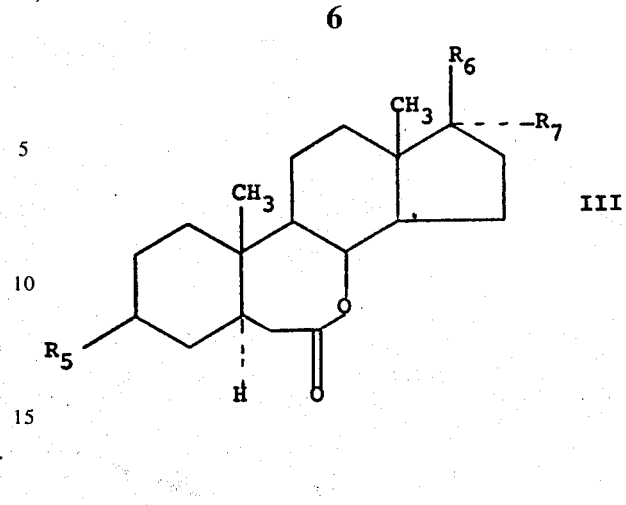

III wherein $R_5$ is lower alkylenedioxy; $R_6$ is hydroxy or acetyl ketalized in the 20-position with lower alkylenedioxy; $R_7$ is hydrogen, lower alkyl, hydroxy, with the proviso that at least one of $R_6$ and $R_7$ is other than hydroxy.

The intermediate of formula III can be prepared by the following reaction scheme:

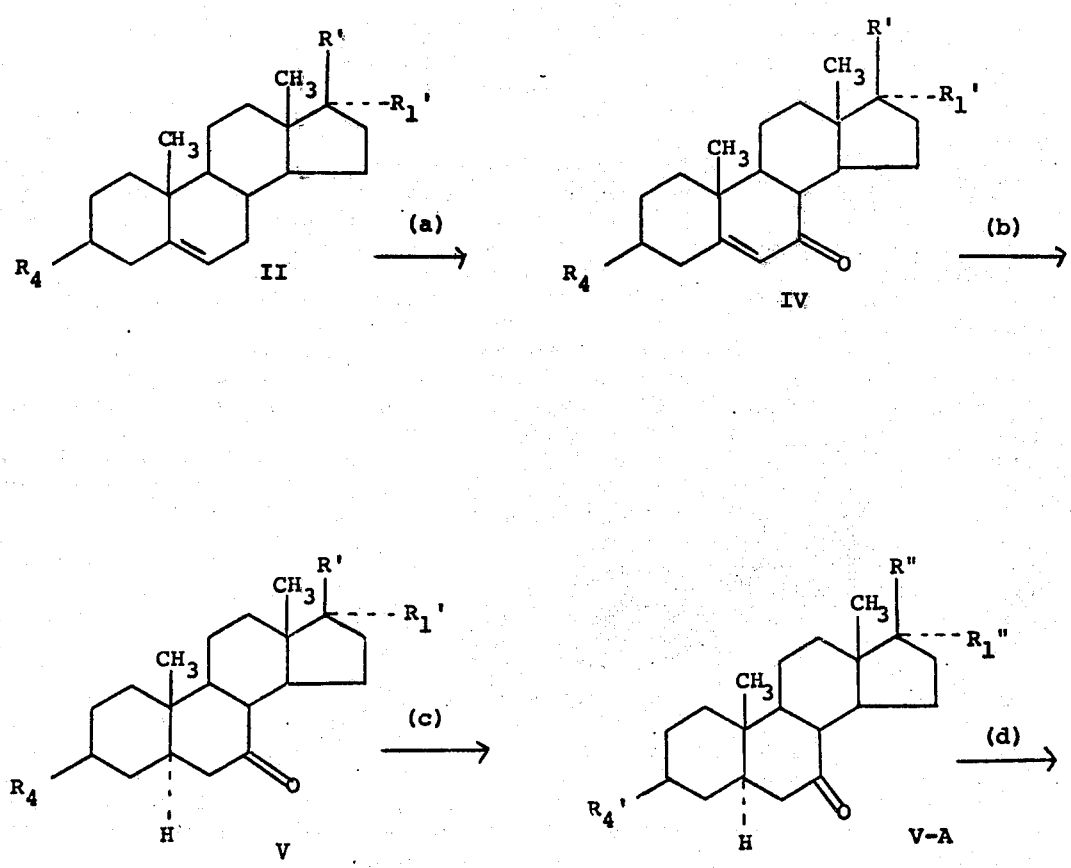

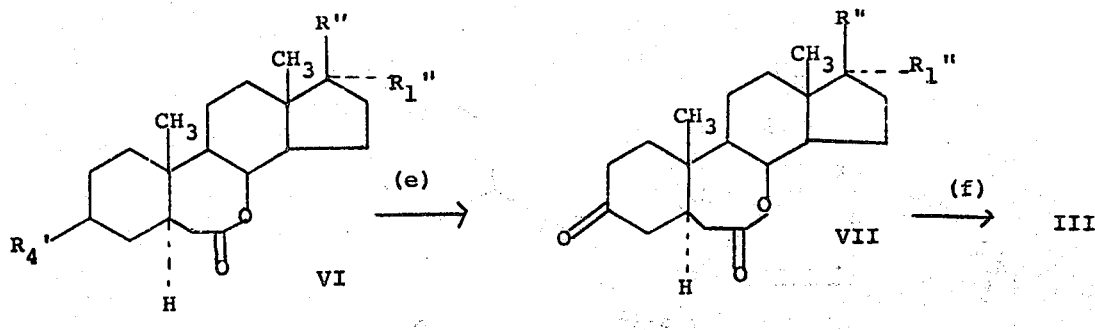

wherein R', R₁', R₄, R₅, R₆ and R₇ are as above; R₄' is trifluoroacetyloxy or hydroxy; R'' is acetyl or trifluoroacetyloxy; R₁'' is hydrogen, lower alkyl, or trifluoroacetyloxy; with the proviso that when R'' is trifluoroacetyloxy, R₁'' is hydrogen or lower alkyl.

The compound of formula II is a compound wherein the free hydroxy groups which may be present in the 3 and 17-positions are protected by esterification. In esterifying a compound of formula II which has free hydroxy groups at the 3 and 17-positions, any conventional esterifying agent can be utilized such as a lower alkanoic acid anhydride or halo substituted lower alkanoic acid anhydride. Where the compound to be protected contains a free hydroxy group at both the 3 and 17-position, it is generally preferred to utilize trifluoroacetic acid anhydride as the esterifying agent, since in the latter steps, hydrolysis of the trifluoroacetoxy groups will occur first in the 3-position. Therefore, the use of trifluoroacetic acid anhydride will provide a 3,17-diester which can be selectively hydrolyzed in the latter steps, to a 3-hydroxy-17-trifluoroacetate ester. While other esterifying agents can be utilized, best results for a selective hydrolysis is accomplished by utilizing trifluoroacetic anhydride as the esterifying agent. The esterification reaction is generally carried out in the presence of an amine base, such as pyridine, triethylamine, etc. In carrying out this reaction, temperatures of from −30°C. to 25°C. are generally utilized.

The conversion of compounds of formula II to compounds of the formula IV via reaction step (a) is carried out by treating the compound of the formula IV with a chromate oxidizing agent. Any of the conventional chromate oxidizing agents such as chromium trioxide pyridine complex, sodium chromate, tertiary butyl chromate, etc., can be utilized. Generally, it is preferred to utilize t-butyl chromate as the oxidizing agent. Generally, this reaction is carried out in an inert organic solvent with a halogenated hydrocarbon solvent, such as carbon tetrachloride and methylene chloride being preferred. In carrying out this reaction, temperature and pressure are not critical, and this reaction can be carried out at room temperature and atmospheric pressure or at elevated temperatures and pressures. Generally, it is preferred to carry out this reaction at a temperature of from 20° to 90°C.

The compound of formula IV is converted to the compound of formula V, via reaction step (b), by catalytically hydrogenating the compound of formula IV. Any conventional means of catalytic hydrogenation can be utilized to convert the compound of the formula IV to the compound of formula V. Among the preferred catalysts for use in this reaction are the noble metals such as palladium or platinum. Generally, these noble metals are utilized with a support material such as carbon or charcoal. The preferred catalyst for use in carrying out the reaction of step (b) is palladium on carbon.

When the ester group on the 3 and 17-positions in the compound of formula V is other than trifluoroacetate, the compounds of formula V can be hydrolyzed by conventional means to produce free OH groups at both the 3 and 17-positions. The hydrolyzed compound can be reesterified by conventional means to the compound of formula V-A so that the protecting groups on both the 3 and 17-positions are trifluoroacetate. By providing a trifluoroacetate protecting group, this protecting group is removed, in later steps of this process utilizing very weak conditions without affecting the lactone structure which is present in the compounds in the later steps of the process of this invention.

In the compound of formula V where the hydroxy groups in the 3 and 17-positions are protected by a trifluoroacetate group, the compound of formula V can be selectively hydrolyzed to the compound of formula V-A so that the hydroxy group in the 3-position is free, whereas the hydroxy group in the 17-position is protected by a trifluoroacetate group.

The compound of formula V-A is converted to the compound of the formula VI via reaction step (d), by Baeyer-Villager oxidation with an organic peracid. Any conventional organic peracid can be utilized in carrying out this oxidation. Among the conventional organic peracids are included peracetic acid, perphthalic acid, etc., with m-chloroperbenzoic acid being preferred. Generally, this reaction is carried out at temperatures from 10°C. to reflux in an inert organic solvent. Any conventional inert organic solvent can be utilized. The preferred inert organic solvents are the halogenated hydrocarbon solvents with chloroform being especially preferred.

The compound of formula VI where R₄' is trifluoroacetoxy can be hydrolyzed with a weak base such as an alkali metal bicarbonate to convert $R_4'$ into a free hydroxy group. The use of a weak base will selectively hydrolyze only the 3-trifluoroacetate group.

The compound of formula VI wherein $R_4'$ is hydroxy is converted to the compound of formula VII by oxidizing the compound of formula VI with the Jones Reagent. Any of the conditions conventionally utilized in Jones Reagent oxidation can be utilized in this reaction.

The compound of formula VII, when reacted with ketalizing agent such as a lower alkylene glycol in the presence of an acid catalyst such as para-toluene sulfonic acid produces a compound of the formula III wherein the 3-oxo group is ketalized. If the compound of formula VII has a 20-oxo group, these groups are also ketalized in this reaction. In carrying out the reaction of step (f), any conventional lower alkylene glycol such as ethylene glycol, propylene glycol, etc., can be utilized as the ketalizing agent. The reaction of step (f) is carried out by utilizing conventional ketalizing procedures well known in the art.

Where $R''$ in the compound of formula VII is trifluoroacetyloxy, the compound of formula VII is hydrolyzed in the aforementioned manner after ketalization to produce a compound of the formula III where $R_6$ is hydroxy.

If during the ketalization reaction of step (f), the 7-oxo group on the compound of formula III becomes ketalized, this ketal group can be selectively removed by treatment with magnesium sulfate in an inert organic solvent wetted with water.

In accordance with this invention, the compound of formula III is converted to a compound of the formula:

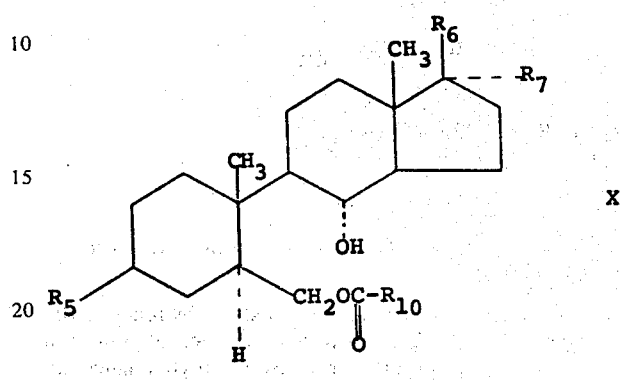

wherein $R_5$, $R_6$ and $R_7$ are as above; and $R_{10}$ is phenyl or lower alkyl.

When $R_{10}$ is lower alkyl, the compound of formula X is prepared via the following reaction scheme:

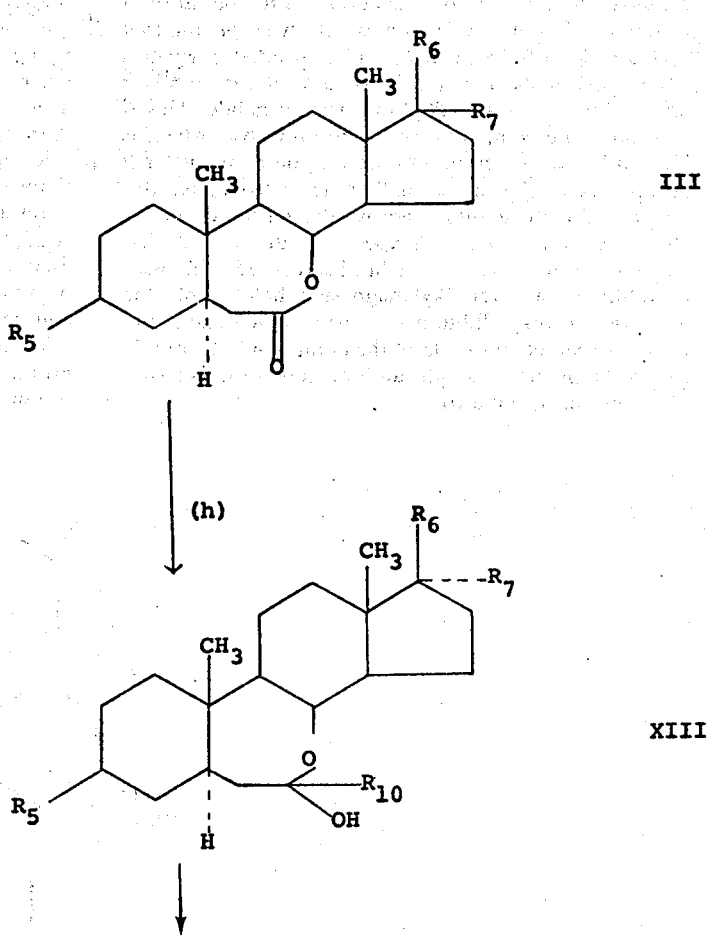

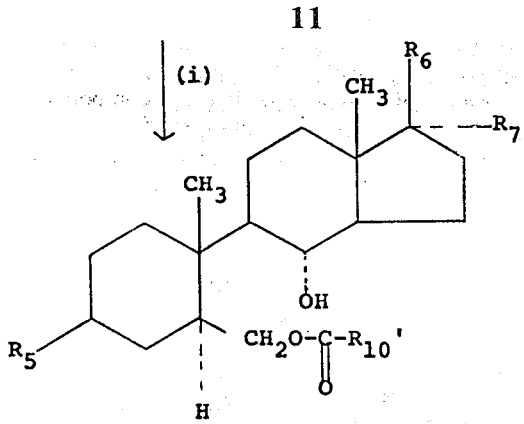

wherein $R_5$, $R_6$ and $R_7$ are as above; and $R_{10}'$ is lower alkyl.

The reaction of step (h) is carried out by reacting the compound of the formula III with a lower alkyl lithium such as methyl lithium or a lower alkyl magnesium halide.

The reactions of step (h) are suitably conducted in an inert organic solvent such as, for example, hydrocarbon ethers, such as tetrahydrofuran, diethyl ether, dioxane or the like, or aromatic hydrocarbons such as benzene or the like. In carrying out the reaction of step (h), temperature and pressure are not critical, and the reaction can be carried out at room temperature and atmospheric pressure. However, if desired, elevated or reduced temperatures can be utilized. Generally, it is preferred to carry out this reaction at a temperature of from −10°C. to +20°C. It is particularly surprising that a compound of the formula XIII is produced when a compound of the formula III is reacted with a lower alkyl lithium or lower alkyl magnesium halide. This is true since the compound of the formula XIII which is formed by this reaction, contains a potential carbonyl group which could additionally react with phenyl lithium to produce addition across the carbonyl group. However, it has been unexpectedly discovered that when the compound of formula III is reacted with lower alkyl lithium or lower alkyl magnesium halide, only one mole of the alkyl lithium or lower alkyl magnesium halide is reacted per mole of the compound of formula III, producing only a single addition across the 7-carbonyl group of formula III.

The compound of the formula XIII is converted to the compound of formula X-A by treating the compound of the formula XIII with an organic peracid. Any conventional organic peracid can be utilized in carrying out this reaction. Among the conventional organic peracids which can be utilized are included perbenzoic acid, m-chloroperbenzoic acid, peracetic acid and monoperphthalic acid. In accordance with a perferred embodiment, monoperphthalic acid is utilized to carry out the reaction of step (i), since oxidation with monoperphthalic acid produces the compound of formula X-A directly form the compound of formula XIII without any undesired side products. It has been found that when other organic peracids are utilized to oxidize the compound of formula XIII to X-A, the compound of formula X-A is formed in combination with other side products. These side products can be separated from the compound of formula X-A by conventional separating techniques such as chromatography. However, when monoperphthalic acid is utilized as the oxidizing agent, only the compound of formula X-A is formed, thereby eliminating the necessity for separating any side products. In carrying out the reaction of step (i), temperature and pressure are not critical and any temperature of from 0° to 100°C. can be utilized. If desired, the reaction of step (i) can be carried out in an inert organic solvent. Any of the conventional inert organic solvents, such as those mentioned hereinbefore can be utilized.

Where $R_{10}$ in the compound of formula X is a phenyl group, the compound of formula X is prepared via the following reaction steps:

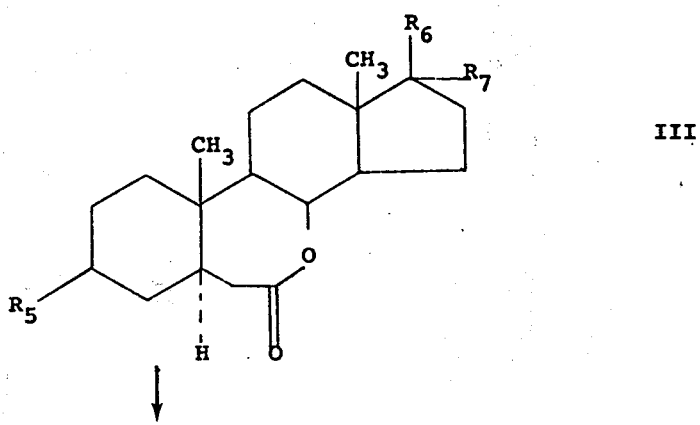

III

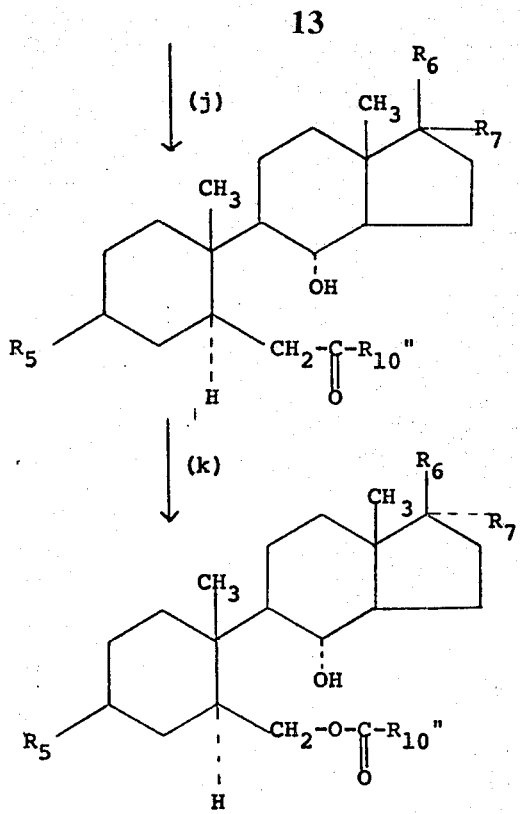

wherein $R_5$, $R_6$ and $R_7$ are as above; and $R_{10}''$ is phenyl.

The compound of formula XV is prepared via reaction step (j) by reacting the compound of formula III with phenyl lithium or a phenyl magnesium halide.

The reaction of step (j) is carried out in the same manner utilizing the same reaction conditions that were described in connection with step (h). The reaction of a compound of the formula III with phenyl lithium or phenyl magnesium halide to produce a compound of the formula XV was surprising, since the phenyl lithium or the phenyl magnesium halide only reacts once with the carbonyl group in the compound of the formula III. No reaction occurred between the phenyl lithium or phenyl magnesium halide and the carbonyl group in the compound of the formula XV. Therefore, by reacting phenyl lithium or phenyl magnesium halide with a compound of the formula III, only one mole of phenyl lithium or phenyl magnesium halide reacts with one mole of the compound of the formula III to produce a compound of the formula XV.

The compound of the formula XV is reacted with organic peracid via reaction step (k) to produce a compound of the formula X-B. The reaction of step (k) is carried out in the same manner and utilizing the same conditions as described in connection with reaction step (i). In carrying out this reaction, monoperphthalic acid is the preferred organic peracid since its use prevents the formation of any undesired side products.

The compound of the formula X above can be converted to the compound of formula I above where $R_2$ is hydrogen and $R_3$ is lower alkylenedioxy by the following reaction scheme:

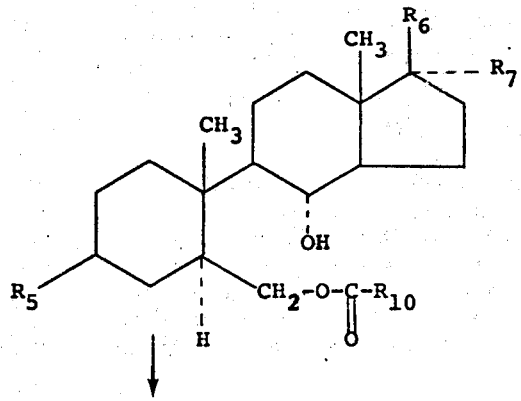

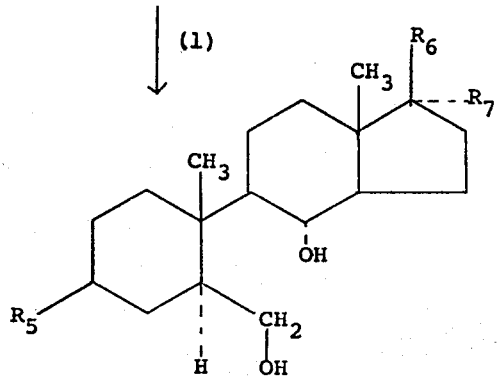

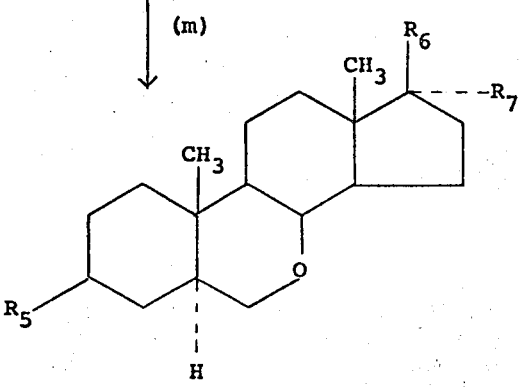

wherein $R_5$, $R_6$ and $R_7$ are as above.

The compound of formula X above is converted to the compound of formula XVI above via reaction step (l) by ester hydrolysis. Any conventional method of ester hydrolysis can be utilized in carrying out the reaction of step (l). Generally, it is preferred to utilize a strong base such as an alkali metal hydroxide to carry out this hydrolysis.

The compound of formula XVI above is converted to the compound of formula XVII by reacting the compound of formula XVI with a compound of the formula:

$R_{11}'$ halo        XVIII wherein $R_{11}'$ is phenyl sulfonyl, lower alkyl sulfonyl and lower alkyl substituted phenyl sulfonyl.

Among the compounds of formula XVIII, tosyl chloride and methane sulfonyl chloride are preferred. The reaction of step (m) is carried out by reacting the compound of formula XVI above with the compound of formula XVIII above in a basic reaction medium. In accordance with a preferred embodiment of this invention, this reaction is carried out in an organic amine base such as triethylamine, pyridine, etc. The organic amine base can act as the solvent medium for the reaction. In carrying out this reaction, temperature and pressure are not critical and this reaction can be carried out at room temperature and atmospheric pressure. Generally, it is preferred to carry out this reaction at a temperature of from 0° to 30°C.

If, in the compound of formula XVII, $R_6$ is a ketalized acetyl group, this ketalized acetyl compound can, if desired, be converted to the corresponding 20-keto compound without effecting the ketal group on the 3-position by treating the compound of formula XVI or XVII above with a weak acid at temperatures of from −20°C. to 20°C. Among the weak acids, oxalic acid or a Lewis acid such as boron trifluoride is preferred. Generally, this reaction is carried out in an inert organic solvent. Any conventional inert organic solvents such as methanol, ethanol, chloroform, carbon tetrachloride, tetrahydrofuran, etc., can be utilized. If desired, when one of $R_6$ or $R_7$ in the compounds of formula XVII is hydroxy, this hydroxy group can be esterified to form a hydrolyzable ester group in the manner described hereinbefore.

The compound of formula XVII above is converted to a compound of formula I wherein $R_2$ and $R_3$ form an isoxazole or pyrazole ring.

ventional means such as treatment with a strong acid, particularly p-toluene sulfonic acid, sulfuric acid, etc. Furthermore, if R is acetyl, which is ketalized in the 20-position with a lower alkylenedioxy group, treatment with a strong acid produces the compound of formula XIX wherein $R_8$ is acetyl having a free oxo group in the 20-position.

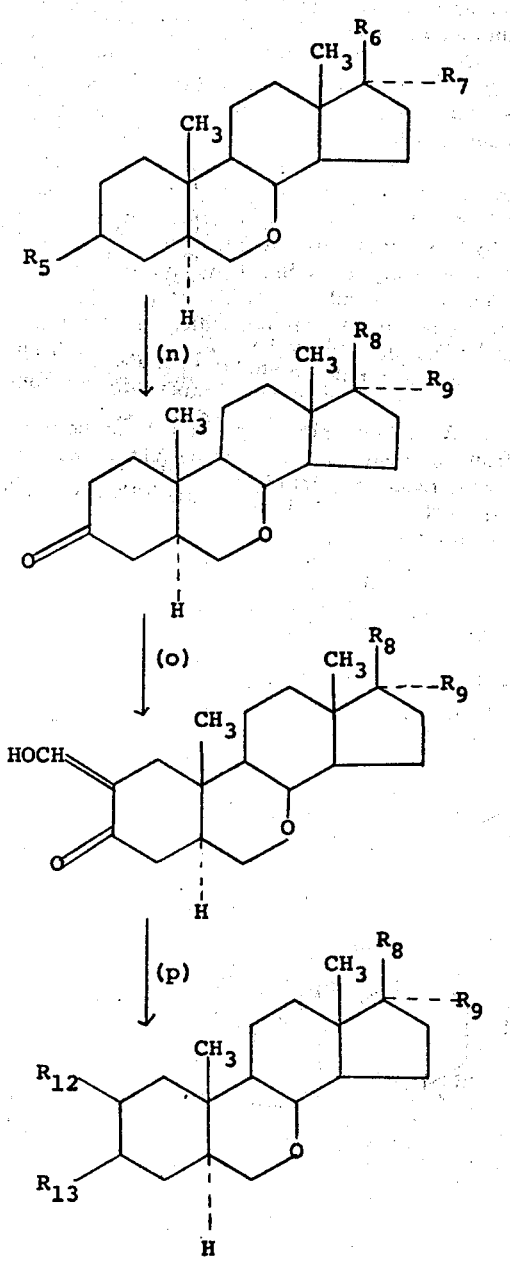

XVII

XIX

XX

XXI wherein $R_6$ and $R_7$ are as above; $R_8$ is hydroxy or acetyl; $R_9$ is hydrogen, hydroxy or lower alkyl with the proviso that one of $R_8$ or $R_9$ is other than hydroxy; and $R_{12}$ and $R_{13}$ taken together with their attached carbon atoms form a pyrazole or isoxazole ring.

In reaction step (n), the ketal group in the 3-position of the compound of formula XVII is cleaved by conventional means such as treatment with a strong acid, The compound of formula XIX above is converted to the compound of formula XX above by treating the compound of formula XIX with a lower alkyl ester of formic acid such as methylformate or ethyl formate. Generally, the reaction of step (o) is carried out in the presence of an alkali metal hydride or an alkali metal lower alkoxide. Any conventional alkali metal hydride such as sodium hydride, potassium hydride, etc., can be utilized. Alternatively, any conventional alkali metal lower alkoxide such as sodium methoxide, potassium ethoxide, etc., can be utilized. This reaction is generally carried out in an inert organic solvent, preferably an organic amine solvent, such as diethylamine, triethylamine, pyridine, etc. In carrying out this reaction, temperature and pressure are not critical and this reaction can be carried out at room temperature and atmospheric pressure. However, if desired, higher or lower temperatures and pressures can be utilized. Generally, this reaction can be carried out at any temperature of from 0°C. to the reflux temperature of the reaction medium.

When $R_{12}$ and $R_{13}$ in the compound of formula XXI form with their attached carbon atoms a pyrazole ring, this compound can be prepared by reacting the compound of formula XX with hydrazine hydrate. Generally, this reaction can be carried out in an inert organic solvent. Any conventional inert organic solvent can be utilized carrying out this reaction. Among the preferred inert organic solvents are included lower alkanol solvents such as methanol, ethanol, etc.; and hydrocarbon solvents such as benzene, toluene, etc. In carrying out this reaction, temperature and pressure are not critical and this reaction can be carried out at room temperature and atmospheric pressure. Generally, this reaction is carried out in any temperature of from 20°C. to the reflux temperature of the reaction medium.

When $R_{12}$ and $R_{13}$ in the compound of formula XXI form an isoxazole ring with the nitrogen adjacent the 3-position, this compound is formed by reacting the compound of the formula XX with an acid addition salt of hydroxylamine utilizing an organic amine base, such as pyridine as the solvent. On the other hand, where $R_{12}$ and $R_{13}$ in the compound of formula XXI form an isoxazole ring with the oxygen adjacent the 3-position, this compound is formed by reacting the compound of formula XX with an acid addition salt of hydroxylamine utilizing a lower alkanoic acid such as acetic acid as the solvent. Generally, the alkali metal salt of the lower alkanoic acid is present in the reaction medium in combination with the alkanoic acid. In forming the isoxazole derivative of formula XXI, pyridine is the preferred organic amine base. Among the preferred salts of hydroxylamine are included the sulfuric acid and hydrochloric acid salts. In carrying out the reaction to produce the isoxazole derivative of formula XXI, temperature and pressure are not critical and this reaction can be carried out at any temperature of from 20°C. to the reflux temperature of the reaction medium.

A $\Delta^4$ and $\Delta^{1,4}$ compound of formula I-A can be produced from the compound of formula XIX above via the following reaction scheme:

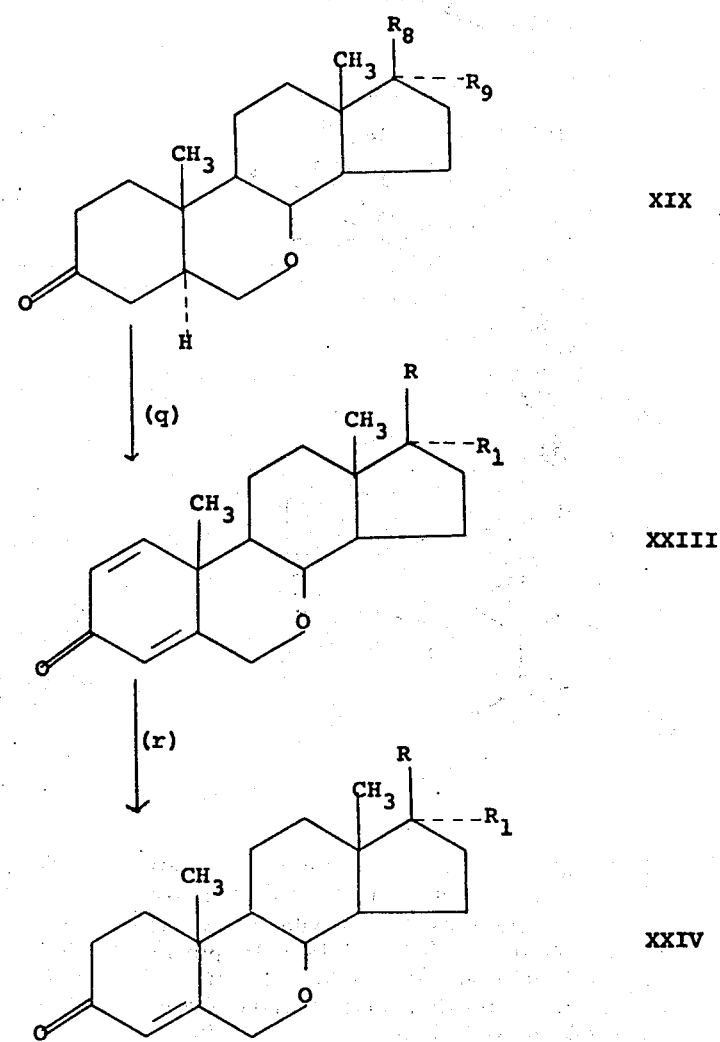

wherein R, $R_1$, $R_8$ and $R_9$ are as above.

The compound of formula XIX is converted to the compound of the formula XXIII by conventional means such as treating the compound of formula XIX with a dehydrogenating agent such as dichlorodicyanobenzoquinone (DDQ). Prior to converting the compound of formula XIX-A to the compound of the formula XXIII, any free hydroxy groups contained within the substituent $R_8$ or $R_9$ should be esterified. The esterification can be carried out by conventional means. If desired, these ester protecting groups can be removed from the compound of formula XXIII of treating the compound of formula XXIII in the conventional manner with an alkali metal base such as sodium hydroxide, potassium hydroxide, sodium bicarbonate, etc. If desired, the oxo groups such as at the 3 and 20-positions in the compound of formula XXIII, can be ketalized to form a 3 and 20-lower alkylenedioxy derivative of the compound of formula XXIII. This ketalization can be carried out in the manner described hereinbefore.

The compound of formula XXIII can be converted to the compound of formula XXIV by hydrogenation utilizing a soluble catalyst such as tristriphenylphosphine chlororhodium. Any of the conditions conventional in hydrogenation can be utilized in carrying out the conversion of compounds of the formula XXIII to the compound of the formula XXIV. If desired, the oxo groups such as at the 3 and 20-positions in the compound of formula XXIV can be ketalized in the manner described hereinbefore to form a 3 and 20-lower alkylenedioxy derivative of the compound of the formula XXIII.

The compounds of formula XIX, XX, XXI, where one of $R_8$ or $R_9$ is a hydroxy group can be esterified with a conventional hydrolyzable ester protecting group as described hereinbefore. On the other hand, where $R_8$ in the compound of formula XIX or XX is acetyl, the 20-oxo group can, if desired, be ketalized by conventional means such as described hereinbefore. The 3-oxo group in the compounds of formulae XIX and XX can, if desired, be ketalized by conventional means.

The following examples are illustrative but not limitative of the present invention. In the examples, all temperatures are in degress centigrade and the ether is diethyl ether.

EXAMPLE 1

Preparation of
3β,17β-dihydroxy-17α-methylandrost-5-ene, 3,17-ditrifluoroacetate To a stirred solution of 3β,17β-dihydroxy-17α-methylandrost-5-ene (80 g.) in dry pyridine (750 ml.) previously cooled to 0° was added trifluoroacetic anhydride (100 ml.) at such a rate that the temperature did not exceed 0°–5°. The reaction mixture was maintained at ice bath temperature for an additional sixty minutes then it was poured slowly into an ice water mixture (3 liters) containing 37% by weight aqueous hydrochloric acid (750 ml.). The off-white precipitate was removed by filtration washed well with water and air dried to give 3β,17β-dihydroxy-17α-methylandrost-5-ene, 3,17-ditrifluoroacetate, m.p. 136°–138°C.

EXAMPLE 2

Preparation of
3β,17β-dihydroxy-17α-methylandrost-5-en-7-one, 3,17-ditrifluoroacetate To a stirred solution of 3β,17β-dihydroxy-17α-methylandrost-5-ene, 3,17-ditrifluoroacetate (39.5 g.) in carbon tetrachloride (400 ml.) containing acetic acid (75 ml.) and acetic anhydride (20 ml.) at 60° was added a mixture of t-butyl chromate in carbon tetrachloride (250 ml.; equivalent to 46 g. of $CrO_3$), acetic acid (75 ml.) and acetic anhydride (20 ml.). The mixture was stirred at 60°–70° for 18 hours then cooled to room temperature filtered and the filtrate added slowly to a stirred solution of oxalic acid (100 g.) in water (1 liter). After 30 minutes, the layers were separated and the organic layer was washed with water twice and brine twice. The dried ($Na_2SO_4$) organic extracts were percolated through a short column of silica gel and then evaporated to give 3β,17β-dihydroxy-17α-methylandrost-5-en-7-one, 3,17-ditrifluoroacetate, as a crude product. This product was crystallized from 100 ml. of a diethylether-hexane mixture (1 to 4 parts by volume) to give 3β,17β-dihydroxy-17α-methylandrost-5-en-7-one, 3,17-ditrifluoroacetate, m.p. 145°–148°C.

EXAMPLE 3

Preparation of
3β,17β-dihydroxy-17α-methyl-5α-androstan-7-one, 17-trifluoroacetate A solution of 3β,17β-dihydroxy-17α-methylandrost-5-en-7-one, 3,17-ditrifluoroacetate (61 g.) in ethyl acetate (500 ml.) was hydrogenated over 4.5 g. of 10% by weight of palladium on charcoal (t=22°, p=760 mm/Hg). After the absorption of 1 equivalent of hydrogen (about 1 hour) the rate of hydrogenation decreased markedly and the reaction was stopped. The catalyst was removed by filtration through diatomaceous silica and the filtrate was evaporated to dryness to give 62 g. of a colorless oil that resisted attempts to crystallize it. The reduced material was dissolved in a mixture of methanol (300 ml.) and tetrahydrofuran (100 ml.) and a solution of potassium bicarbonate (35 g.) in water (100 ml.) was added. The mixture was stirred for 60 minutes then diluted with water and extracted with methylene chloride. The combined organic layers were dried ($MgSO_4$), evaporated to dryness and the residue was crystallized from methylene chloride-hexane (1 to 4 parts by volume) to give 3β,17β-dihydroxy-17α-methyl-5α-androstan-7-one, 17-trifluoroacetate, m.p. 164°–166°C.

EXAMPLE 4

Preparation of
3β,17β-dihydroxy-17α-methyl-7a-oxa-5α-B-homoandrostan-7-one, 17-trifluoroacetate A solution of 3β,17β-dihydroxy-17α-methyl-5α-androstan-7-one, 17-trifluoroacetate (39 g.) and m-chloroperbenzoic acid (85%, 40 g.) in chloroform was heated under reflux for 3 hours. The reaction mixture was cooled to room temperature then washed with 5% by weight aqueous sodium bisulfite solution twice, with saturated sodium bicarbonate solution twice and with water once. The combined organic layers were dried (Na$_2$SO$_4$), evaporated and the residue crystallized from methylene chloride diethyl ether (1 to 4 parts by volume) to give 3β,17β-dihydroxy-17α-methyl-7a-oxa-5α-B-homoandrostan-7-one, 17-trifluoroacetate, m.p. 187°–188°C.

EXAMPLE 5

Preparation of
17β-hydroxy-17α-methyl-7a-oxa-5α-B-homoandrostane-3,7-dione, 17-trifluoroacetate A solution of 3β,17β-dihydroxy-17α-methyl-7a-oxa-5α-B-homoandrostan-7-one, 17-trifluoroacetate (39 g.) in acetone (100 ml.) was cooled to 0°. To the stirred solution Jones' reagent* (40 ml.) was added and the reaction mixture was allowed to stir at 0°–5° for 5 minutes. Isopropanol (50 ml.) was added and the reaction was stirred for an additional 5 minutes. The reaction mixture was diluted with water (4 liters) and the resulting precipitate was collected by filtration then dissolved in methylene chloride, dried (MgSO$_4$), and evaporated in vacuo to give 17β-hydroxy-17α-methyl-7a-oxa-5α-B-homoandrostane-3,7-dione, 17-trifluoroacetate.

*chromic acid and sulfuric acid in water

EXAMPLE 6

Preparation of
17β-hydroxy-17α-methyl-7a-oxa-5α-B-homoandrostane-3,7-dione, 3-ethylene ketal, 17-trifluoroacetate A solution of 17β-hydroxy-17α-methyl-7a-oxa-5α-B-homoandrostane-3,7-dione, 17-trifluoroacetate (2.4 g.) and p-toluenesulfonic acid (100 mg.) in benzene (30 ml.) containing ethylene glycol (2.4 ml.) heated under reflux for 3 hours. The water was removed as it was formed by means of a Dean-Stark trap. The mixture was cooled and poured into an ice cold sodium bicarbonate solution. The layers were separated and the organic layer was washed with brine, then dried (Na$_2$SO$_4$) and concentrated to dryness. The resulting residue was crystallized from methanol to give 17β-Hydroxy-17α-methyl-7a-oxa-5α-B-homoandrostane-3,7-dione, 3-ethylene ketal, 17-trifluoroacetate, m.p. 187°–188°C.

EXAMPLE 7

Preparation of
17β-hydroxy-17α-methyl-7a-oxa-5α-B-homoandrostane-3,7-dione, 3-ethylene ketal To a stirred solution of 17β-hydroxy-17α-methyl-7a-oxa-5α-B-homoandrostane-3,7-dione, 3-ethylene ketal, 17-trifluoroacetate (27 g.) in tetrahydrofuran previously cooled to 0° was added 57 ml. of a 1N sodium hydroxide solution. A sufficient amount of methanol was added to make the reaction homogenous and after 5 minutes 10ml. of ethyl acetate was added. The reaction mixture was concentrated in vacuo to ~100 ml. and then was diluted with water. The resulting precipitate was collected by filtration, then washed with water and air dried. Crystallization from diethyl ether-hexane (1 to 5 parts by volume) afforded 17β-hydroxy-17α-methyl-7a-oxa-5α-B-homoandrostane-3,7-dione, 3-ethylene ketal, m.p. 211°–212°C.

EXAMPLE 8

Preparation of
5-(2-benzoylmethyl-4,4-ethylenedioxy-1-methyl-1-cyclohexanyl)-1,7α-dimethylhexahydroindan-1,4-diol To a stirred solution of 17β-hydroxy-17α-methyl-7a-oxa-5α-B-homoandrostane-3,7-dione, 3-ethylene ketal (13.3 g.) in dry tetrahydrofuran (400 ml.) previously cooled to 0° was added 48 ml. of a 2N solution of phenyl lithium in benzene diethyl ether (75:25 by volume). The ice bath was removed and the mixture was allowed to stir at room temperature for 60 minutes then it was poured over ice and extracted with ethyl acetate. The organic layers were washed with water, then dried (Na$_2$SO$_4$) and evaporated to give a colorless oil. Filtration through a short column of Alumina (Woelm, neutral, grade III) furnished 5-(2-benzoylmethyl-4,4-ethylenedioxy-1-methyl-1-cyclohexanyl)-1,7α-dimethylhexahydroindan-1,4-diol.

EXAMPLE 9

Preparation of
5-(2-benzoyloxymethyl-4,4-ethylenedioxy-1-methyl-1-cyclohexanyl)-1,7α-dimethylhexahydroindan-1,4-diol To a solution of 5-(2-benzoylmethyl-4,4-ethylenedioxy-1-methyl-1-cyclohexanyl)-1,7α-dimethylhexahydroindan-1,4-diol (15 g.) in chloroform (500 ml.) was added 250 ml. was added 250 ml. of a 0.5 N solution of monoperphthalic acid in diethyl ether. The mixture was allowed to stand at room temperature for three hours then was washed with 1N sodium hydroxide solution and with brine. The dried (MgSO$_4$) organic layers were evaporated to give 5-(2-benzoyloxymethyl-4,4-ethylenedioxy-1-methyl-1-cyclohexanyl)-1,7α-dimethylhexahydroindan-1,4-diol as an oil. Chromatography on a column of silica gel (300 g.) furnished 5-(2-benzoyloxymethyl-4,4-ethylenedioxy-1-methyl-1-cyclohexanyl)-1-7α-dimethylhexahydroindan-1,4-diol as a pure product.

EXAMPLE 10

Preparation of
5-(2-hydroxymethyl-4,4-ethylenedioxy-1-methyl-1-cyclohexanyl)-1,7α-dimethylhexahydroindan-1,4-diol A solution of 5-(2-benzoyloxymethyl-4,4-ethylenedioxy-1-methyl-1-cyclohexanyl)-1,7α-dimethylhexahydroindan-1,4-diol (10 g.) in ethanol (400 ml.) containing 15 ml. of 10 N sodium hydroxide was heated under reflux for 18 hours. The reaction mixture was concentrated in vacuo then diluted with water and extracted with methylene chloride. The combined organic layers were washed with brine, dried over Na$_2$SO$_4$ and concentrated to dryness to give 5-(2-hydroxymethyl-4,4-ethylenedioxy-1-methyl-1-cyclohexanyl)-1,7α-dimethylhexhydroindan-1,4-diol.

EXAMPLE 11

Preparation of
7-oxa-17β-hydroxy-17α-methyl-5α-androstan-3-one, 3-ethylene ketal A solution is prepared by dissolving 7.5 g. of 5-(2-hydroxy methyl-4,4-ethylenedioxy-1-methyl-1-cyclohexanyl)-1,7α-dimethylhexahydroindan-1,4-diol in dry pyridine (75 ml.) and p-toluenesulfonyl chloride (7.5 g.) was added. The solution was stirred at room temperature for 4 hours then was poured in an ice-water mixture containing 75 ml. of concentrated hydrochloric acid. The resulting mixture was quickly extracted with methylene chloride and the organic layers were washed with 1N aqueous sodium hydroxide solution and with brine. The dried (MgSO$_4$) organic extracts were evaporated to give 7.2 g. of a solid that was essentially homogenous by tlc. Two crystallizations from methanol gave the pure 7-oxa-17β-hydroxy-17α-methyl-5α-androstan-3-one, 3-ethylene ketal, m.p. 199°–200°C.

EXAMPLE 12

Preparation of
1,5-dihydroxy-8,8-ethylenedioxy-1,5,10α,12α-tetramethyl
per-hydro-1H-benz[d]-indeno-[4,5-b]-oxepin To a stirred solution of 17β-hydroxy-17α-methyl-7α-oxa-5α-B-homoandrostane-3,7-dione, 3-ethylene ketal (16.0 g.) in dry tetrahydrofuran (400 ml.) previously cooled to 0° was added 110 ml. of a 1.9 M solution of methyl lithium in diethyl ether. The cooling was removed and the mixture was allowed to stir at ambient temperature for 15 minutes, then it was poured over ice and extracted with ethyl acetate. The organic extracts were washed with water, dried (Na$_2$SO$_4$) and evaporated to give 1,5-dihydroxy-8,8-ethylenedioxy-1,5,10α,12α-tetramethyl per hydro-1H-benz-[d]-indeno-[4,5-b]-oxepin as a white solid.

EXAMPLE 13

Preparation of
5-(2-hydroxymethyl-4,4-ethylenedioxy-1-methyl-1-cyclohexanyl)-1,7α-dimethylhexahydroindan-1,4-diol To a solution of 1,5-dihydroxy-8,8-ethylenedioxy-1,5,10α,12α-tetramethyl per hydro-1H-benz-[d]-indeno-[4,5-b]-oxepin (15.7 g.) in chloroform (400 ml.) was added 400 ml. of a 0.65 N solution of monoperphthalic acid in diethyl ether. The mixture was allowed to stand at room temperature for 3 hours then was washed with a 1N sodium hydroxide solution and with brine. The combined organic extracts were dried (MgSO$_4$) and evaporated in vacuo to give 5-(2-acetoxymethyl-4,4-ethylenedioxy-1-methyl-1-cyclohexanyl)-1,7α-dimethylhexahydroindan-1,4-diol as a colorless oil.

A solution of 5-(2-acetoxymethyl-4,4-ethylenedioxy-1-methyl-1-cyclohexanyl)-1,7α-dimethylhexahydroindan-1,4-diol (12.3 g.) in ethanol (500 ml.) containing 20 ml. of 10N sodium hydroxide was refluxed overnight. The reaction mixture was concentrated in vacuo then diluted with water and extracted with methylene chloride. The combined organic layers were washed with water, dried (Na$_2$SO$_4$) and evaporated under reduced pressure to give 5-(2-hydroxymethyl-4,4-ethylenedioxy-1-methyl-1-cyclohexanyl)-1,7α-dimethylhexahydroindan-1,4-diol.

EXAMPLE 14

Preparation of
7-oxa-17β-hydroxy-17α-methyl-5α-androstan-3-one

A solution of 7-oxa-17β-hydroxy-17α-methyl-5α-androstan-3-one, 3-ethylene ketal (61 g.) in tetrahydrofuran (800 ml.) and 1N aqueous hydrochloric acid (100 ml.) was allowed to stand at room temperature for 18 hours. The reaction mixture was concentrated, diluted with water and the resulting solids were filtered, washed with water and dried to give 52.3 g. of 7-oxa-17β-hydroxy-17α-methyl-5α-androstan-3-one. Crystallization of a small amount from methylene chloride diethyl-ether gave the analytically pure material, mp. 186°–188°C.

EXAMPLE 15

Preparation of
7-oxa-2-hydroxymethylene-17β-hydroxy-17α-methyl-5α-androstan-3-one To a solution of 7-oxa-17β-hydroxy-17α-methyl-5α-androstan-3-one (4.1 g.) in dry pyridine (90 ml.) was added freshly distilled ethyl formate (7.5 ml.) followed by freshly prepared sodium methoxide (1.38 g.). The reaction mixture was stirred at room temperature overnight then was poured into ice and water containing acetic acid (75 ml.). The resulting mixture was extracted with methylene chloride (3 × 100 ml.). The combined organic layers were washed once with water and then 6 times with 100 ml. portions of a 2% potassium hydroxide solution. The combined basic extracts were washed once with diethyl-ether and then were acidified with acetic acid (20 ml.). The resulting slightly yellow precipitate was washed with water and air dried to give a crude product. Crystallization of this crude product from benzene-hexane (1 to 4 parts by volume) (using methylene chloride to initially dissolve the material) gave the 7-oxa-2-hydroxymethylene-17β-hydroxy-17α-methyl-5α-androstan-3-one, m.p. 235°–238°C.

EXAMPLE 16

Preparation of
7-oxa-17β-hydroxy-17α-methyl-5α-androstano-[3,2-c]-pyrazole

A solution of 7-oxa-2-hydroxymethylene-17β-hydroxy-17α-methyl-5α-androstan-3-one (2.7 g.) in ethanol (100 ml.) containing hydrazine hydrate (0.65 ml. of or 85% by weight aqueous solution) was heated under reflux for 60 minutes. The solvent was removed in vacuo and the resulting solid was triturated with methylene chloride to give 7-oxa-17β-hydroxy-17α-methyl-5α-androstano-[3,2-c]-pyrazole, m.p. 263°–267°C.

EXAMPLE 17

7-Oxa-17β-hydroxy-17α-methyl-5αandrostan-3-one, 3-ethylene ketal

Tablet Formulation

| 7-oxa-17β-hydroxy-17α-methyl-5α-androstan-3-one, 3-ethylene ketal | Per Tablet |
|---|---|
| 7-oxa-17β-hydroxy-17α-methyl-5α-androstan-3-one, 3-ethylene ketal | 2.55 mg. |
| Dicalcium phosphate, unmillilled | 232.45 mg. |
| Corn Starch | 12.50 mg. |
| Magnesium Stearate | 2.50 mg. |
| Total Weight | 250.00 mg. |

Procedure:

1. 7-oxa-17β-hydroxy-17α-methyl-5α-androstan-3-one, 3-ethylene ketal and corn starch were blended in a suitable size mixer.

2. The mix was then blended with an equal quantity of Dicalcium Phosphate.

3. The mixture was blended for 5 minutes with the balance of the Dicalcium Phosphate and magnesium stearate.

4. The mixture was then compressed.

EXAMPLE 18

Tablets were prepared in the same manner as in Example 17 except that 7-oxa-17β-hydroxy-17α-methyl-5α-androstano-[3,2-c]-pyrazole was utilized as the active ingredient.

EXAMPLE 19

7-oxa-17β-hydroxy-17α-methyl-5α-androstan-3-one, 3-ethylene ketal

Suppository Formulation

| | Per 1.3 Gm. Suppository |
|---|---|
| 7-oxa:17β-hydroxy-17α-methyl-5α-androstan-3-one, 3-ethylene ketal | 0.005 gm. |
| Wecobee M[1] | 1.250 gm. |
| Carnauba Wax | 0.045 gm. |

[1]cocoa butter — coconut derived fat having a melting point of 96°F.

Procedure:

1. The Wecobee M and the carnauba wax were melted in a suitable size glass lined container (stainless steel may also be used), mixed well and cooled to 45°C.
2. 7-oxa-17β-hydroxy-17α-methyl-5α-androstan-3-one, 3-ethylene ketal, which had been reduced to a fine powder with no lumps, was added and stirred until completely and uniformly dispersed.
3. The mixture was poured into suppository molds to yield suppositories having an individual weight of 1.3 gms.
4. The suppositories were cooled and removed from molds. They were individually wrapped in wax paper for packaging. (Foil may also be used.)

EXAMPLE 20

A suppository was formed in the same manner as in Example 19 except that 7-oxa-17β-hydroxy-17α-methyl-5α-androstano-[3,2-c]-pyrazole was utilized as the active ingredient.

EXAMPLE 21

7oxa-17β-hydroxy-17α-methyl-5α-androstan-3-one, 3-ethylene ketal

Capsule Formulation

| | Per Capsule |
|---|---|
| 7-oxa-17β-hydroxy-17α-methyl-5α-androstan-3-one, 3-ethylene ketal | 5 mg. |
| Lactose | 178 mg. |
| Corn Starch | 37 mg. |
| Talc | 5 mg. |
| Total Weight | 225 mg. |

Procedure:

1. 7-oxa-β-hydroxy-17α-methyl-5α-androstan-3-one, 3-ethylene ketal was mixed with the lactose and corn starch in a suitable mixer.
2. The mixture was further blended by passing through a Fitzpatrick Comminuting Machine with a No. 1A screen with knives forward.
3. The blended powder was returned to the mixer, the talc added and blended thoroughly. The mixture was then filled into No. 4 hard shell gelatin capsules on a Parke Davis capsulating machine.

EXAMPLE 22

A capsule was formed in the same manner as Example 21 except that 7-oxa-17β-hydroxy-17α-methyl-5α-androstano-[3,2-c]-pyrazole was utilized as the active ingredient.

EXAMPLE 23

7-oxa-17β-hydroxy-17α-methyl-5α-androstan-3-one, 3-ethylene ketal 0.1% Cream

| | Mg. Per Gram |
|---|---|
| 7-oxa-17β-hydroxy-17α-methyl-5α-androstan-3-one, 3-ethylene ketal | 1.00 |
| Stearyl Alcohol | 100.0 |
| Cetyl Alcohol | 15.00 |
| White Petrolatum | 70.00 |
| Methyl Parahydroxybenzoate, U.S.P. | 2.00 |
| Propyl Parahydroxybenzoate, U.S.P. | 0.50 |
| Isopropyl Palmitate | 60.00 |
| Polyoxyl 40 Stearate, U.S.P. | 40.00 |
| Propylene Glycol | 120.00 |
| Disodium Versenate | 0.10 |
| Distilled Water | 597.16 |

Procedure:

1. The stearyl alcohol, cetyl alcohol, petrolatum, propyl parahydroxybenzoate, isopropyl palmitate and polyoxyl 40 stearate were melted at 75°C. The mixture was cooled to and maintained at 70°C.
2. Disodium versenate and methyl parahydroxybenzoate were dissolved in hot distilled water to which was added the propylene glycol. The solution was mixed at 75°C. and slowly added to the oil solution prepared previously, using slow agitation. The emulsion was gradually cooled with slow stirring.
3. When the temperature of the ointment reached 55°C., a solution of 7-oxa-17β-hydroxy-17α-methyl-5α-androstan-3-one, 3-ethylene ketal was added and mixed with the ointment.
4. When the temperature of the ointment reached 50°C., cold water was circulated in the jacket of the kettle and the ointment was cooled to 30°C. with stirring. The ointment was then transferred to storage containers.

EXAMPLE 24

A 0.1% cream was prepared in the same manner as Example 23 except that 7-oxa-17β-hydroxy-17α-methyl-5α-androstano-[3,2-c]-pyrazole was utilized as the active ingredient.

EXAMPLE 25

Preparation of
3β,17α-dihydroxy-5α-pregnan-7,20-dione diacetate

A solution of 45.73 g. of 3β,17α-dihydroxypregn-5-en-7,20-dione diacetate in 1 1. of ethyl acetate and 5 ml. of pyridine containing 5 g. of 10% by weight palladium on charcoal was shaken in a hydrogen atmosphere at room temperature for 9 hours. The catalyst was removed by filtration through charcoal and the filtrate was concentrated in vacuo to yield a solid. Two crystallizations from methylene chloride-methanol gave 3β,17α-dihydroxy-5α-pregnan-7,20-dione diacetate.

EXAMPLE 26

Preparation of
3β,17α-dihydroxy-5α-pregnan-7,20-dione

To a solution of 39.6 g. of 3β,17α-dihydroxy-5α-pregnan-7,20-dione diacetate in 600 ml. of dioxane and 500 ml. of methanol under a nitrogen atmosphere at room temperature was added 450 ml. of 1.0 N sodium hydroxide dropwise over 30 minutes. After stirring at room temperature for 3½ hours, 200 ml. of 3 N HCl was added and most of the solvent was removed in vacuo. Water was added and the resultant solid was filtered and air dried to give 3β,17α-dihydroxy-5α-pregnan-7,20-dione.

EXAMPLE 27

Preparation of
3β,17α-dihydroxy-5α-pregnan-7,20-dione bistrifluoroacetate

To 0.7007 g. of 3β,17α-dihydroxy-5α-pregnan-7,20-dione in 10 ml. of anhydrous pyridine cooled in an ice bath was added 0.87 ml. of trifluoroacetic anhydride. After stirring for 1 hour at 3°, the yellow solution was added dropwise to 10 ml. of concentrated HCl and ice with stirring. The resultant solid was removed by filtration, dissolved in benzene and passed through a column of 16 g. of silica gel. Elution with 200 ml. of 5% by volume ethyl acetate in benzene and concentration of the eluent in vacuo gave a solid. Crystallization from methylene chloride diethyl ether gave 0.753 g. of 3β,17α-dihydroxy-5α-pregnan-7,20-dione bistrifluoroacetate.

EXAMPLE 28

Preparation of
3β,17α-dihydroxy-7-a-oxa-5α-B-homopregnan-7,20-dione bistrifluoroacetate To 0.822 g. (1.5 mmole) of 3β,17α-dihydroxy-5α-pregnan-7,20-dione bistrifluoroacetate in 20 ml. of chloroform was added 0.609 g. (3 mmole) of meta-chloroperbenzoic acid.

After standing at room temperature for 64 hours, 40 ml. of 10% sodium sulfite solution was added and stirred for 15 minutes. The organic layer was separated and washed with 5% by weight aqueous sodium bicarbonate solution, dried (MgSO₄) and concentrated in vacuo. Crystallization from methylene chloride ether gave 3β,17α-dihydroxy-7a-oxa-5α-B-homopregnan-7,20-dione bistrifluoroacetate.

EXAMPLE 29

Preparation of
3β,17α-dihydroxy-7a-oxa-5α-B-homopregnan-7,20-dione

To 0.590 g. of 3β,17α-dihydroxy-7a-oxa-5α-B-homopregnan-7,20-dione bistrifluoroacetate dissolved in 5 ml. of dioxane and 10 ml. of methanol was added 0.64 g. of potassium bicarbonate in 4 ml. of water. After stirring for 40 minutes, 10 ml. of water was added and most of the solvent was removed in vacuo. Water was added and the crystalline solid was removed by filtration and air dried to yield 3β,17α-dihydroxy-7a-oxa-5α-B-homopregnan-7,20 dione.

EXAMPLE 30

Preparation of
17α-hydroxy-7a-oxa-5α-B-homopregnan-3,7,20-trione

Chromium trioxide (0.669 g.) was added in portions to 1.5 ml. of anhydrous pyridine and 50 ml. of methylene chloride with stirring at room temperature. After stirring for 15 minutes, 0.331 g. of 3β,17α-dihydroxy-7a-oxa-5α-B-homopregnan-7,20 -dione in 50 ml. of methylene chloride was added and the reaction mixture was stirred for 30 minutes. The dark solution was washed with water, with 1N HCl, dried (MgSO₄) and the solution was passed through a column of 2 g. of silica gel. Elution with 100 ml. of methylene chloride and then with 100 ml. of 30% by volume ethyl acetate in benzene and concentration of the combined eluent gave a solid. Crystallization from ethyl acetate gave 17α-hydroxy-7a-oxa-5α-B-homopregnan-3,7,20-trione.

EXAMPLE 31

Preparation of
17α-hydroxy-3,3-7,7-20,20-trisethylenedioxy-7a-oxa-5α-B-homopregnane A solution of 0.1316 g. of 17α-hydroxy-7a-oxa-5α-B-homopregnan-3,7,20-trione in 50 ml. of anhydrous benzene, 0.4 ml. of ethylene glycol and 5.2 mg. of p-toluenesulfonic acid monohydrate was stirred and refluxed under a Dean-Stark water separator filled with molecular sieve 4A for 47 hours. The reaction mixture was washed with 5% sodium bicarbonate solution, dried (Na₂SO₄) and concentrated in vacuo. Crystallization from methylene chloride diethyl ether gave 17α-hydroxy-3,3-7,7-20, 20-trisethylenedioxy-7a-oxa-5α-B-homopregnane.

EXAMPLE 32

Preparation of
17α-hydroxy-3,3-20,20-bisethylenedioxy-7a-oxa-5α-B-homopregnan-7-one A solution of 0.130 g. of 17α-hydroxy-3,3-7,7-20,20-trisethylenedioxy-7a-oxa-5α-B-homopregnane in 100 ml. of benzene saturated with water was stirred at room temperature with 10 g. of anhydrrous magnesium sulfate for 2 hours, filtered and concentrated in vacuo. Crystallization from methylene chloride-ether-hexane gave 17α-hydroxy-3,3-20,20-bisethylenedioxy-7a-oxa-5α-B-homopregnan-7-one.

EXAMPLE 33

Preparation of
17α-hydroxy-3,3-20,20-bisethylenedioxy-7a-oxa-5α-pregnane

To 1.98 g. (4.4 mmole) of 17α-hydroxy-3,3-20,20-bisethylenedioxy-7a-oxa-5α-B-homopregnan-7-one in 150 ml. of anhydrous tetrahydrofuran was added over 20 minutes 13 ml. (21 mmole) of 1.6M methyl lithium in diethyl ether with ice bath cooling under a nitrogen atmosphere. The cooling bath was removed after 15 minutes and stirring was continued at room temperature for 1½ hours. Water (25 ml.) was added dropwise and most of the solvent was removed in vacuo. Water was added and the product which was 1α,5-dihydroxy-8-ethylenedioxy-1-(1,1-ethylenedioxyethyl)-5,10aβ,-12aβ-trimethyl-perhydro-6aβ-benz[d]indeno[4,5-b]oxepin was extracted with ethyl acetate, dried (MgSO$_4$) and concentrated in vacuo to yield a solid. 1α,5-dihydroxy-8-ethylenedioxy-1-(1,1-ethylenedioxyethyl)-5,10aβ,12aβ-trimethylperhydro-6aα-benz[d]indeno[4,5-b]oxepin was dissolved in 50 ml. of chloroform and 18 ml. of 0.73M monoperphthalic acid in diethyl ether was added. The mixture was stirred at room temperature for 1½ hours, filtered to remove the precipitated perphthalic acid, the filtrate was washed with saturated sodium bicarbonate solution, dried (Na$_2$SO$_4$) and concentrated to yield 1β-(1,1-ethylenedioxyethyl)-5-(2-acetoxymethyl-4,4-ethylenedioxy-1-methylcyclohexanyl)-7aβ-methyl-3a,4,5,6,7,7a-hexahydroindan-1α,4α-diol as a solid. This solid was dissolved in 80 ml. of ethanol and 3.5 ml. of 10N sodium hydroxide solution was added. The solution was refluxed for 40 hours and then concentrated in vacuo. Water was added and the product was extracted with methylene chloride, dried (MgSO$_4$) and concentrated to yield a foam (1.78 g.). The crude product was dissolved in 20 ml. of anhydrous pyridine and treated at room temperature with 2.0 g. of p-toluenesulfonyl chloride. After stirring at room temperature for 4 hours, ice was added slowly in small pieces to hydrolyze the excess p-toluenesulfonyl chloride. Most of the pyridine was removed at ~ 1 mm, water was added and the resultant solid was filtered and washed with water. The solid was dissolved in methylene chloride, dried (MgSO$_4$) and concentrated in vacuo to a yellow solid. Crystallization from methylene chloride-ether gave 17α-hydroxy-3,3-20,20-bisethylenedioxy-7a-oxa-5α-pregnane, m.p. 198°–206°C.

EXAMPLE 34

Preparation of
17α-hydroxy-7-oxa-5α-pregnan-3,20-dione

A solution of 50 mg. of 17α-hydroxy-3,3-20,20-bisethylenedioxy-7-oxa-5α-pregnane in 2 ml. of methanol and 0.30 ml. of aqueous 8% sulfuric acid ($^v/_v$) was refluxed for 10 hours. The solution was concentrated to dryness in vacuo, water was added and the product was extracted with methylene chloride, the extract was dried (MgSO$_4$), concentrated in vacuo and the product crystallized from methylene chloride-diethyl-ether to yield 17α-hydroxy-7-oxa-5α-pregnan-3,20-dione.

EXAMPLE 35

Preparation of
17α-hydroxy-7-oxapregna-1,4-diene-3,20-dione
acetate

To a solution of 37 mg. of 17α-hydroxy-7-oxa-5α-pregnan-3,20-dione in 5 ml. of dioxane was added 50 mg. of dichlorodicyanobenzoquinone and 1 mg. of p-toluenesulfonic acid and the solution was heated at reflux for 5 hours. The cooled reaction mixture was diluted with methylene chloride and washed three times with 1N aqueous sodium hydroxide and then with water. The extract was dried (MgSO$_4$) and concentrated in vacuo to yield the 17α-hydroxy-7-oxapregna-1,4-diene-3,20-dione which was acetylated by treatment at room temperature with 2.4 ml. of acetic anhydride and 0.01 ml. of 72% by weight perchloric acid in 25 ml. of anhydrous ethyl acetate. The solution was left at room temperature for 15 minutes washed with 5% by weight aqueous sodium bicarbonate solution, dried (MgSO$_4$) and concentrated in vacuo. Crystallization of the crude product from methylene chloride-diethyl ether gave 17α-hydroxy-7-oxapregna-1,4-diene-3,20-dione acetate.

EXAMPLE 36

Preparation of
17α-hydroxy-7-oxapregn-4-en-3,20-dione acetate

A solution of 50 mg. of 17α-hydroxy-7-oxapregna-1,4-diene-3,20-acetate in 5 ml. of 20% by volume ethanol in benzene and 15 mg. of tris-triphenylphosphine rhodium chloride was stirred in a hydrogen atmosphere at room temperature for 6 hours. The solvent was removed in vacuo and the crude product was dissolved in benzene and filtered through a column of 0.5 g. of neutral alumina. The benzene eluent was concentrated in vacuo and the product crystallized from methylene chloride-diethyl-ether to give 17α-hydroxy-7-oxapregn-4-en-3,20-dione acetate.

EXAMPLE 37

To a solution of 7-oxa-17β-hydroxy-17α-methyl-5α-androstan-3-one (1.0 g.) in dry pyridine (7 ml.) previously cooled to 0°C. was added trifluoroacetic anhydride (1.0 ml.). The reaction mixture was stirred at 0°–5° for 30 minutes then was poured into an ice water mixture and acidified with 3N hydrochloric acid. The resulting precipitate was collected by filtration and washed with water and then was dissolved in methylene chloride. The dried solution (Na$_2$SO$_4$) was evaporated in vacuo to give 7-oxa-17β-hydroxy-17α-methyl-5α-androstan-3-one, 17-trifluoroacetate.

EXAMPLE 38

To a solution of 7-oxa-17β-hydroxy-17α-methyl-5α-androstan-3-one, 17-trifluoroacetate (3.0 g.) in dioxane (65 ml.) containing p-toluenesulfonic acid (10 mg.) was added dichlorodicyanobenzoquinone (3.6 g.) and the solution was heated under reflux for 5 hours. The cooled reaction mixture was diluted with methylene chloride (~ 200 ml.) and the precipitated hydroquinone was removed by filtration. The filtrate was washed three times with 1N aqueous sodium hydroxide solution and then with water. The combined organic extracts were dried (Na$_2$SO$_4$) and evaporated to give 2.2 g. of an oil which was then dissolved in methanol (50 ml.) containing 10 ml. of 1N sodium hydroxide solution. After 60 minutes at room temperature, the reaction mixture was diluted with water and extracted with methylene chloride. The organic layers were washed with water, dried (Na$_2$SO$_4$) and concentrated in vacuo to give 1.6 g. of a pale yellow foam. Crystallization of the residue from methanol furnished 7-oxa-17β-hydroxy-17α-methylandrosta-1,4-dien-3-one, m.p. 183°–185°C.

EXAMPLE 39

Preparation of
7-oxa-17β-hydroxy-17α-methylandrostano [2,3d] isoxazole

To a solution of 7-oxa-2-hydroxymethylene-17α-methyl-5α-androstan-3-one (2.7 g.) in acetic acid (25 ml.) was added a solution of hydroxylamine hydrochloride (0.565 g.) and anhydrous sodium acetate (0.66 g.) in water (2 ml.). The reaction mixture was heated at 95°–100°C. for 30 minutes then cooled and the resulting precipitate was collected and washed with acetic acid-water (4:1 parts by volume) and then water. The dried solid was triturated with methylene chloride to give 7-oxa-17β-hydroxy-17α-methylandrostano [2,3d] isoxazole, mp. 302°–303°C.

EXAMPLE 40

Preparation of 7-oxa-17β-hydroxy-17α-methylandrostano [3,2c] isoxazole

To a solution of 7-oxa-2-hydroxymethylene-17α-methyl-5α-androstan-3-one (2.7 g.) in pyridine (10 ml.) was added a solution of hydroxylamine hydrochloride (1.13 g.) in water (2 ml.) The resulting solution was refluxed for 3 hours then cooled and the solvent removed in vacuo. The residue was dissolved in ethyl acetate and the organic solution was washed in turn with 1N hydrochloric acid and water, then dried ($Na_2SO_4$) and concentrated to dryness. The crude material (2.4 g.) was dissolved in dry tetrahydrofuran (250 ml.) and sodium methoxide (1.0 g.) was added. After standing at room temperature for 60 minutes, the organic solution was washed with saturated brine solution then dried ($Na_2SO_4$) and evaporated in vacuo. Crystallization of the residue from acetone furnished 7-oxa-17β-hydroxy-17α-methylandrostano [3,2c]isoxazole, mp. 290-292°C.

EXAMPLE 41

Preparation of 7-oxa-17β-hydroxy-17α-methyl-5α-androstane

A solution of 7-oxa-17β-hydroxy-17α-methyl-5α-androstan-3-one (3.4 g.) and (3.4 g.) p-toluenesulfonyl hydrazide in methanol (150 ml.) was heated at reflux for 2 hours. The solution was cooled and sodium borohydride (6 g.) was added portionwise, then the reaction mixture was brought to reflux for 5 minutes. Water (10 ml.) was added to the cooled solution which was then concentrated in vacuo. The residual solid was dissolved in methylene chloride and the organic solution was washed in turn with 1N hydrochloric acid, 1N sodium hydroxide and brine then dried ($Na_2SO_4$) and evaporated to give crude 7-oxa-17β-hydroxy-17α-methyl-5α-androstane. Crystallization from methanol gave the pure material, mp. 175°–176°C.

EXAMPLE 42

Preparation of 7-oxa-3β,17β-dihydroxy-17α-methyl-5α-androstane

To a mixture of lithium tri-t-butoxyaluminum hydride (3.0 g.) in dry tetrahydrofuran (15 ml.) previously cooled to 0°–5°C was added a solution of 7-oxa-17β-hydroxy-17α-methyl-5α-androstan-3-one in dry tetrahydrofuran (25 ml.). After 10 minutes, water (20 ml.) was added and most of the solvent removed in vacuo. The product was extracted with ethyl acetate and the organic solution was washed with water, dried ($Na_2SO_4$) and evaporated under reduced pressure. Crystallization of the residue from diethyl ether afforded 1.2 g. of 7-oxa-3β,17β-dihydroxy-17α-methyl-5α-androstane, m.p. 174°–175°C.

EXAMPLE 43

Preparation of 7-oxa-3β,17β-dihydroxy-17α-methyl-5α-androstane, 3-acetate

A solution of 7-oxa-3β,17β-dihydroxy-17α-methyl-5α-androstane in pyridine (5 ml.) containing acetic anhydride (2 ml.) was allowed to stand at room temperature for 16 hours then was diluted with water. The resulting solid was collected by filtration, washed with water and dried. Crystallization of the product from diethyl ether furnished 7-oxa-3β,17β-dihydroxy-17α-methyl-5α-androstane 3-acetate, m.p. 148°–149°C.

We claim:

1. A compound of the formula:

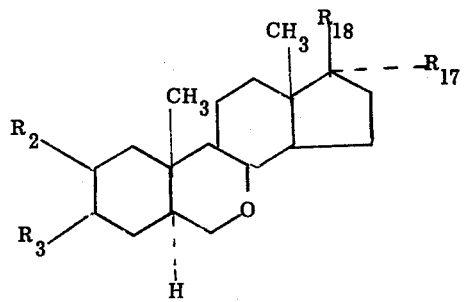

wherein $R_2$ and $R_3$ are taken togther to form a pyrazole ring; $R_{18}$ is hydroxy or hydroxy esterified with a lower alkanoic acid or a halo lower alkanoic acid, with said alkanoic acid containing from 2 to 7 carbon atoms.

2. The compound of claim 1 wherein said compound is 7-oxa-17β-hydroxy-17α-methyl-5α-androstano [3,2c]-pyrazole.

* * * * *